(12) United States Patent
Flegal et al.

(10) Patent No.: US 6,410,310 B1
(45) Date of Patent: Jun. 25, 2002

(54) CELL CULTURE EXPANSION PLATE

(75) Inventors: Philip B. Flegal; Richard E. Gould, both of Santa Rosa, CA (US)

(73) Assignee: Alta Biotech, Inc., Santa Rosa, CA (US)

( * ) Notice: Subject to any disclaimer, the term of this patent is extended or adjusted under 35 U.S.C. 154(b) by 0 days.

(21) Appl. No.: 09/539,471

(22) Filed: Mar. 30, 2000

(51) Int. Cl.[7] .................................................. C12M 1/22
(52) U.S. Cl. ............................ 435/305.2; 435/288.4; 422/102; 220/555
(58) Field of Search ..................... 435/288.4, 305.2, 435/305.3; 422/102; 356/246; 220/555

(56) References Cited

U.S. PATENT DOCUMENTS

| | | | |
|---|---|---|---|
| 3,491,875 A | * | 1/1970 | Fischer et al. |
| 3,787,290 A | * | 1/1974 | Kaye |
| 4,010,078 A | * | 3/1977 | Taylor |
| 5,106,297 A | * | 4/1992 | Discko, Jr. |
| 5,753,456 A | * | 5/1998 | Naqui et al. |

FOREIGN PATENT DOCUMENTS

| WO | WO-99/54711 A1 | * | 10/1999 |
|---|---|---|---|

\* cited by examiner

*Primary Examiner*—William H. Beisner
(74) *Attorney, Agent, or Firm*—Johnson & Stainbrook, LLP; Larry D. Johnson; Craig M. Stainbrook

(57) ABSTRACT

An improved cell culture plate for in vitro cultivation of cells and/or tissue cultures, the cell culture plate comprising a base member and a flat removable lid, the base having the external dimensions of a standard cell culture plate and further having multiple sets of open-topped wells. Each set of wells comprises two or more wells of increasing area and volume, and the collection of sets are preferably arranged in side-by-side columns, each column being adapted for use in cell or tissue culture expansion. The sizing and configuration of the wells enables cell culture expansion through the use of a single cell culture plate, rather than through use of a series of plates having wells of increasing size and volume.

2 Claims, 1 Drawing Sheet

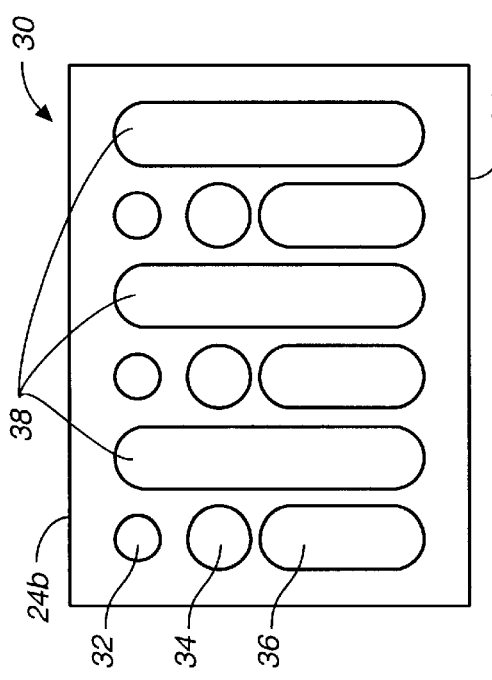
FIG._3
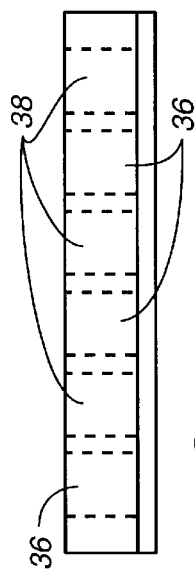
FIG._4
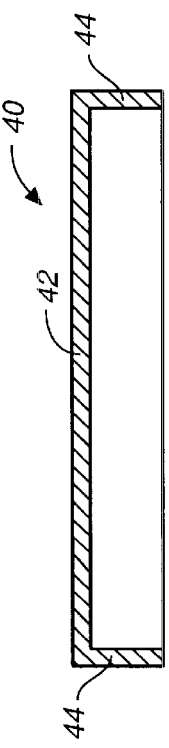
FIG._5
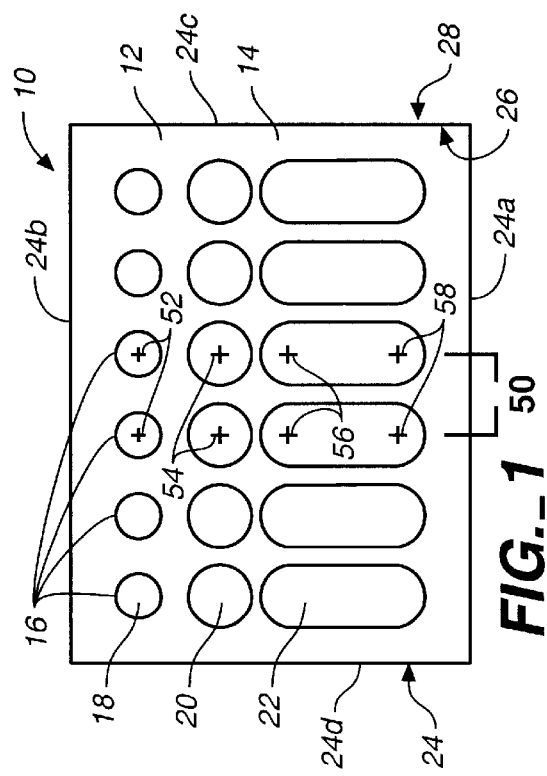
FIG._1
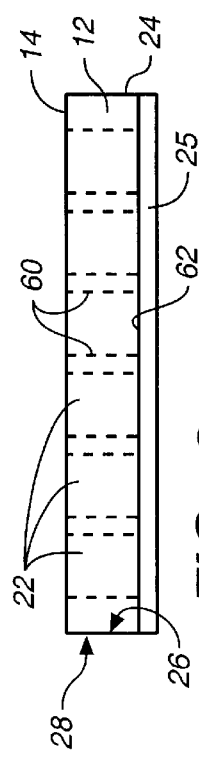
FIG._2

CELL CULTURE EXPANSION PLATE

BACKGROUND OF THE INVENTION

1. Field of the Invention

The present invention relates generally to cell culture plates, and more particularly to a cell culture plate with multiple sets of wells, each set comprising two or more wells of increasing size and volume for cell or tissue culture expansion.

2. Description of Related Art

Numerous branches of biology, including the fields of immunology, microbiology, parasitology, pharmacology, toxicology, biotechnology, and biomedical engineering, routinely require large populations of pure cell or tissue cultures. Cell culturing is conducted on nutrient media in Petri dishes or, more commonly, in conventional cell culture plates having uniform well sizes. Separating, isolating, and then expanding cells or microorganisms thus typically entails transferring multiple cultures from cell culture plates with uniform well sizes to other plates having uniform well sizes with larger well volumes. At present, once cell cultures are established in a culturing medium on a cell culture plate, they are transferred from plates having 2 mL volume wells to plates with 5 mL wells, and thereafter to plates with wells having volumes greater than 5 mL, and so forth. In consequence, lab technicians and research scientists are required to monitor numerous plates for a single cell culture.

It would be desirable to have a cell culture plate having least two or more open-topped wells of increasing area and volume. This would eliminate the need to transfer cell cultures to new plates for culture expansion and would further eliminate the need to track numerous plates for a single culture. Multi-well culture plates have been devised, but existing designs serve different ends and comprise different structures. For example, U.S. Pat. No. 5,578,490 to Ubeira discloses a cell culture plate with a system for lateral diffusion of molecules across a barrier membrane. The plate comprises a lid, fit to cover a base consisting of two or more flat-bottomed open-topped wells, denominated the reservoir wells, each containing one or more smaller, open-topped diffusion wells sharing the same base as the reservoir wells. The diffusion wells communicate with the larger reservoir well which houses it via one or several slits located in the lateral walls of the diffusion wells, each slit being covered by a semipermeable membrane that permits the passage of soluble substances while retaining insoluble particles and cells. This solves the problem caused by other cell culture plates wherein the diffusion of substances occurs between a higher compartment and a lower compartment, and the two compartments are separated by a barrier membrane; in this situation microscopic observation and manipulation of the cells is difficult. However, the invention disclosed in the '490 patent does not solve the problem of having to transfer expanding cell cultures to plates having wells with greater volume.

U.S. Pat. No. 5,972,694 to Mathis discloses a cluster plate having a plurality of non-removable wells for growing cells in vitro for use in large scale drug transport studies. The plate combines a device for supporting tissue cultures in a fluid medium with a structure that allows unfettered access to the portion of the well below the tissue culture. That is, the wells have an upper chamber and a lower chamber separated by a microporous membrane. Adjacent to each well is an access port having a separate opening in the top surface of the plate that provides direct access to the lower chamber of the corresponding well. The access port provides communication between the lower chamber and the ambient environment. The lower chamber is of a greater cross sectional area than the combined cross sectional areas of the upper chamber and the access port.

Though having a plurality of differentially sized wells, the '694 patent does not disclose a method or an apparatus for cell culture expansion using a single cell culture plate. Accordingly, there remains a need for a cell culture plate specifically designed and adapted for cell culture expansion using a single cell culture plate.

SUMMARY OF THE INVENTION

Accordingly, the present invention is an improved cell culture plate for in vitro cultivation of cells and/or tissue cultures, said cell culture plate comprising a base member and a flat removable lid, the base having the external dimensions of a standard cell culture plate and further having multiple sets of open-topped wells. Each set of wells comprises two or more wells of increasing area and volume, and the collection of sets are preferably arranged in side-by-side columns, each column being adapted for use in cell or tissue culture expansion. The sizing and configuration of the wells enables cell culture expansion through the use of a single cell culture plate, rather than through use of a series of plates having wells of increasing size and volume.

BRIEF DESCRIPTION OF THE DRAWINGS

FIG. 1 is a top plan view of a first preferred embodiment of the cell culture plate of the present invention;

FIG. 2 is a side elevation view of the cell culture plate of FIG. 1;

FIG. 3 is a top plan view of a second preferred embodiment of the cell culture plate;

FIG. 4 is a side elevation view of the cell culture plate of FIG. 3; and

FIG. 5 is a side elevation cross-sectional view of the lid for each of said cell culture plates shown in the foregoing figures.

DETAILED DESCRIPTION OF A PREFERRED EMBODIMENT

FIG. 1 is a top plan view of the first preferred embodiment of the cell culture plate of the present invention. FIG. 2 is a side elevation view of the cell culture plate of FIG. 1., showing the wells in phantom. These views show that the cell culture plate 10 comprises a rectangular base member 12, preferably having width and length dimensions generally conforming to industry standards; viz., a width of approximately 3.5 inches (8.89 cm), and a length of approximately 5.0 inches (12.7 cm). The specific dimensions are not essential to effective cell culturing if the dimensions are within practicable and empirically proven limits. Accordingly, though not essential to effective cell culturing, the plate has a height slightly higher than the industry standard of 0.560 inches (1.42 cm), and instead spans a height of approximately 0.81 inches (2.06 cm).

The base member preferably defines a hollow chamber and includes a top surface 14 and multiple sets of open-topped wells forming depressions into said chamber, each of said sets having at least two wells of increasing area at the top opening and increasing volume. In the first preferred embodiment, each set constitutes a column of wells comprising a first, second, and third well, 18, 20, and 22, respectively, the size of which increases from the first to the third so as to accommodate expanding tissue and/or cell cultures. Preferably the first and second wells have a circular shape when viewed from above, while the third well has an oval shape when similarly viewed. The periphery of each well is defined and bounded at its top by the top surface 14, which is in turn bounded by an integral base member skirt, or surrounding border 24, having interior 26 and exterior 28 surfaces, and said border depending downwardly from said top surface to define the perimeter or edge of the entire cell culture plate. The border is integral with both the top surface 14 and the bottom surface 25 of the cell culture plate, and has a bottom side 24a, a top side, 24b, a right side 24c, and a left side 24d.

In its second preferred embodiment, depicted in FIGS. 3 and 4, the cell culture plate of the present invention 30 again comprises a generally standard sized cell culture plate, and further comprises multiple sets of wells, each having a first, second and third, 32, 34, and 36, respectively, but further includes a fourth well 38 for each of said set of wells. As a cell or tissue culture expands in a smaller well so as to require increased area and volume for further growth, it may be transferred from to the next larger well, and so on until the well sizes are exhausted. This obviates the need for transferring cultures from one culture plate to another, thus saving a researching or technician time, and providing obvious environmental benefits.

Dimensions of the wells may be varied and tailored to the particular culturing procedures undertaken. However, for general cell culture expansion procedures, it has been established that the following dimensions have the desirable characteristics and features indicated above while meeting industry standards: Referring now to FIGS. 1 and 2, in the first preferred embodiment, each set of wells has a center line 50; each of said first wells has a top circumference and a first center 52; each of said second wells has a top circumference and a second center 54; and each of said third wells has a top arc center 56 and a bottom arc center 58 defining the center points for the top and bottom circumferential arcs, respectively, of the third ovoid well of each well column. The distance between well columns, measured center line to center line is preferably 0.750 inches (1.91 cm). The distance between any well perimeter and that of another well is 0.1 inches (0.254 cm), and the same distance extends between that of the plate edge and the well perimeters closest to the plate edge. Measuring from the bottom side 24a of the plate, the distance to the third well bottom arc center 58 is 0.730 inches (1.85 cm); to the top arc center 56, 1.616 inches (4.105 cm); to the second well center 54, 2.345 inches (5.956 cm); and to the first well center 52, 3.075 inches (7.810 cm). Each of the wells has sides 60 depending downwardly and perpendicular to the top and bottom surfaces, a top opening, a depth of 0.689 inches (1.750 cm), and preferably a flat bottom 62. Accordingly, the first and second wells are substantially right cylinders.

The radius of the first well is 0.216 inches (0.549 cm), and, accordingly, has a top opening area of 0.147 in$^2$ (0.947 cm$^2$), and a total volume of 0.101 in$^3$ (1.657 mL). The second well and third well top and bottom arcs have a radius of 0.305 inches (0.775 cm). Accordingly, the second well has a top opening area of 0.292 in$^2$ (1.89 cm$^2$), and a total volume of 0.201 in$^3$ (3.31 mL). The third well has a top opening area of 0.692 in$^2$ (4.47 cm$^2$), and a total volume of 0.477 in$^3$ (7.82 mL).

Referring now to FIGS. 3 and 4, the second preferred embodiment of the cell culture plate of the present invention has dimensions identical to those of the first preferred embodiment, the sole exception being the fourth wells 38, which effectively replace three of the well columns of the first preferred embodiment. The fourth well extends to within 0.1 inch (0.254 cm) from the bottom and top sides, 24a and 24b, respectively, thus extending a length of 3.3 inches (8.38 cm), but otherwise has the same dimensions as the third well. It has a top opening area of 0.821 in$^2$ (5.54 cm$^2$), and a total volume of 0.565 in$^3$ (9.70 mL). The fourth well is suitable for applications requiring a relatively large well.

FIG. 5 is a cross sectional side elevation view of the lid 40 for the cell culture plate of the present invention. The lid has an upper surface 42 and downwardly projecting sides 44 which fit snugly over the exterior surfaces 28 of the surrounding border of the base member.

The cell culture plate may be manufactured by an injection molding process or any suitable means for molding thermoplastic polymers and may be fabricated from either a transparent or an opaque plastic.

While this invention has been described in connection with preferred embodiments thereof, it is obvious that modifications and changes therein may be made by those skilled in the art to which it pertains without departing from the spirit and scope of the invention. Accordingly, the scope of this invention is to be limited only by the appended claims.

What is claimed as invention is:

1. A cell culture expansion plate, comprising:

a base member having a top surface, a bottom surface, a border surrounding and depending downwardly from said top surface to said bottom surface and defining the sides of said base member, and at least one set of three open-topped wells forming depressions in said top surface, each of said sets of wells including a first, a second, and a third well which, from said first well to said third well, are of increasing area at the top opening and are of increasing volume so as to accommodate expanding tissue and/or cell cultures, and wherein said first and second wells of each of said sets have a substantially circular top opening when viewed from above and said third well of each of said sets has a substantially oval shape when similarly viewed.

2. A cell culture expansion plate, comprising:

a base member having a top surface, a bottom surface, a border surrounding and depending downwardly from said top surface to said bottom surface and defining the sides of said base member, and at least one set of four open-topped wells forming depressions in said top surface, including a first, a second, a third, and a fourth well which, from said first well to last, are of increasing area at the top opening and are of increasing volume so as to accommodate expanding tissue and/or cell cultures, and wherein said first and second wells of each of said sets have a substantially circular top opening when viewed from above and wherein each of said remaining wells of each set have substantially oval shapes when similarly viewed.

* * * * *